United States Patent
Bonner et al.

(10) Patent No.: US 10,780,029 B2
(45) Date of Patent: Sep. 22, 2020

(54) TRIPHASIC CLEANSING COMPOSITION

(71) Applicant: Johnson & Johnson Consumer Inc., Skillman, NJ (US)

(72) Inventors: Patricia Bonner, Branchburg, NJ (US); Prithwiraj Maitra, Hillsborough, NJ (US); Donald Lynn Harper, Flemington, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 251 days.

(21) Appl. No.: 15/251,145

(22) Filed: Aug. 30, 2016

(65) Prior Publication Data

US 2017/0087063 A1  Mar. 30, 2017

Related U.S. Application Data

(60) Provisional application No. 62/234,849, filed on Sep. 30, 2015.

(51) Int. Cl.

| *A61K 8/00* | (2006.01) |
|---|---|
| *A61K 8/02* | (2006.01) |
| *A61K 8/03* | (2006.01) |
| *A61Q 19/00* | (2006.01) |
| *A61K 8/34* | (2006.01) |
| *A61K 8/44* | (2006.01) |
| *A61K 8/46* | (2006.01) |
| *A61K 8/60* | (2006.01) |
| *A61K 8/73* | (2006.01) |
| *A61K 8/81* | (2006.01) |
| *A61Q 19/10* | (2006.01) |

(52) U.S. Cl.
CPC .............. *A61K 8/0241* (2013.01); *A61K 8/03* (2013.01); *A61K 8/342* (2013.01); *A61K 8/345* (2013.01); *A61K 8/442* (2013.01); *A61K 8/463* (2013.01); *A61K 8/602* (2013.01); *A61K 8/731* (2013.01); *A61K 8/8152* (2013.01); *A61Q 19/008* (2013.01); *A61Q 19/10* (2013.01); *A61K 2800/28* (2013.01); *A61K 2800/41* (2013.01); *A61K 2800/412* (2013.01)

(58) Field of Classification Search
None
See application file for complete search history.

(56) References Cited

U.S. PATENT DOCUMENTS

| 6,656,487 | B2 | 12/2003 | Afriat et al. | |
|---|---|---|---|---|
| 7,594,619 | B2 | 9/2009 | Ghere, Jr. et al. | |
| 8,258,250 | B2 | 9/2012 | Fevola et al. | |
| 8,399,590 | B2 | 3/2013 | Gardner et al. | |
| 9,364,416 | B2 | 6/2016 | Bonner et al. | |
| 9,370,478 | B2 | 6/2016 | Bonner et al. | |
| 2006/0029625 | A1* | 2/2006 | Niebauer | A61K 8/027 424/401 |
| 2008/0108714 | A1 | 5/2008 | Swazey et al. | |
| 2011/0223125 | A1* | 9/2011 | Hough | A61K 8/8152 424/70.12 |
| 2013/0345105 | A1* | 12/2013 | Carlson | B08B 7/0021 510/103 |
| 2014/0134218 | A1* | 5/2014 | Bonner | A61K 8/0245 424/401 |
| 2015/0040933 | A1 | 2/2015 | Bonner et al. | |
| 2015/0203799 | A1* | 7/2015 | Bettiol | C11D 3/1266 510/235 |
| 2015/0210967 | A1 | 7/2015 | Van Engelen et al. | |

FOREIGN PATENT DOCUMENTS

| EP | 2332519 A | 6/2011 |
|---|---|---|
| WO | WO 2014/142651 A | 9/2014 |

OTHER PUBLICATIONS

International search report and written opinion of the international searching authority dated Oct. 17, 2016, for international application PCT/US2016/049403.
The International Cosmetic Ingredient Dictionary and Handbook, 7th Edition (1997) ("ICI Handbook"), eds. Wenninger and McEwen, The Cosmetic, Toiletry and Fragrance Assoc., Washington, D.C., pp. 1626, 1654-1661.
Sagarin, Cosmetics, Science and Technology, 2nd Edition (1972), vol. 1, pp. 32-43.
Bernhofer, et al., "The Influence of the Response of Skin Equivalent Systems to Topically Applied Consumer Products by Epithelial-Mesenchymal Interactions", *Toxicology* in Vitro, (1999) pp. 219-229.
"Trans-Epithelial Permeability (TEP) Assay" as set forth in Invittox Protocol No. 86 (May 1994).

* cited by examiner

Primary Examiner — Necholus Ogden, Jr.

(57) ABSTRACT

A cleansing composition, a method of making the cleansing composition and a method of using a cleansing composition, the composition including a first liquid surfactant component; a first solid component, including a plurality of cellulose particles; and a first gaseous component.

11 Claims, 2 Drawing Sheets

TRIPHASIC CLEANSING COMPOSITION

This application claims the benefit of U.S. provisional application 62/234,849 filed on Sep. 30, 2015, the complete disclosure of which is hereby incorporated by reference for all purposes.

FIELD OF THE INVENTION

The present invention relates to the use of a particulate cleansing aid to provide enhanced cleaning benefits while maintaining a desired level of mildness. The cleansing aid may include three distinct phases, including a solid, liquid and gaseous phase.

BACKGROUND

It has long been desired to produce a cleaning product that has improved cleansability, with the added benefit of gentle exfoliating of skin. It is additionally desired to achieve such cleansing and exfoliation via nontraditional gently-abrasive 'particulate matter.' Traditional methods of exfoliating have been used, such as adding or increasing concentration of surfactants, polyethylene beads, gycolic acids or combinations thereof.

Traditional methods used to enhance the cleansing benefits of a product (i.e., pumice, polyethylene beads, ground apricot kernels, ground nut shells) are typically known to be harsh/rough upon application on the skin, essentially abrasive. This is typically inherent with the mode of action of the specific particulate used, and are known to cause redness, irritation and potentially disrupt the skin barrier. Over time, the cleansing bases have been developed to be milder, using a cream/lotion like cleanser base instead of a traditional surfactant system; however, the products still contain these harsh abrasive agents, which still cause redness and irritation even with the enhanced mildness of the base. Additional abrasives have been developed to be even milder, but still have a medium risk of irritation. These options also have an undesirable ecological impact, as they are mostly non-biodegradable.

There is a desire for a cleansing composition, or an additive to be used in a cleansing composition, which provides a suitable exfoliation to the skin, is sufficiently mild, and desirably has less of an ecological impact than the aforementioned prior approaches.

BRIEF DESCRIPTION OF THE FIGURES

FIG. 2A is a photograph showing a test subject arm with two make-up spots deposited thereon. FIG. 2B is a photograph showing the results of a test after ten revolutions with a triphasic composition. FIG. 2C is a photograph showing the results of a test after ten revolutions with a biphasic composition.

SUMMARY

Figure 1:
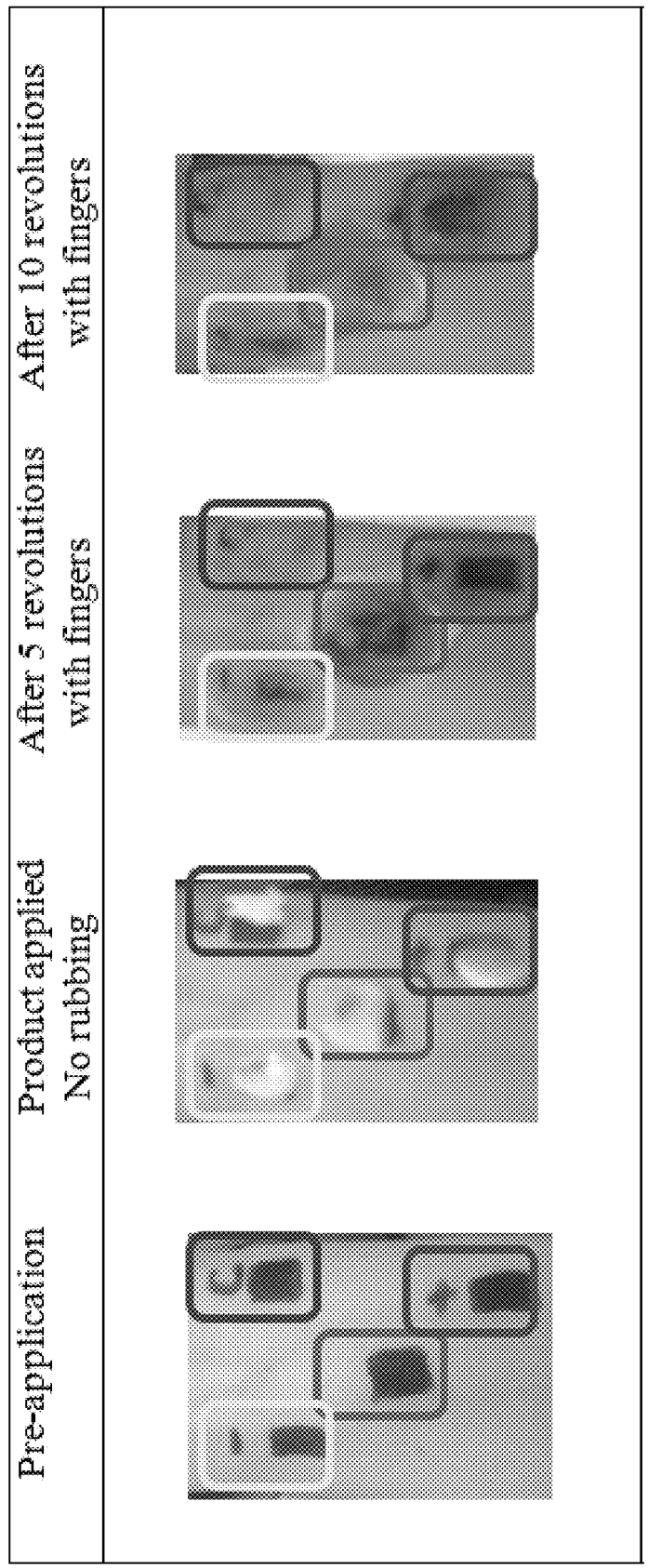
FIG. 1 is a series of photographs showing the results of a test in Example 1.

The present invention includes a cleansing composition, a method of making the cleansing composition and a method of using a cleansing composition. The cleansing composition may include, in some aspects, a first liquid component, including an anionic or nonionic surfactant; a first solid component, including a plurality of cellulose particles; and a first gaseous component; where the first liquid component, the first solid component and the first gaseous component are mixed with each other to provide a substantially homogeneous cleansing composition.

The invention includes, in other aspects, methods of using a cleansing composition to remove at least one undesirable skin element (such as dirt, oil, bacteria, or other matter to be removed from the skin surface). The method may include one or more of the steps of: applying to a target site of the skin surface a composition including: a first liquid component, including an anionic or nonionic surfactant; a first solid component, including a plurality of cellulose particles; and a first gaseous component; where the first liquid component, the first solid component and the first gaseous component are mixed with each other to provide a substantially homogeneous cleansing composition; rubbing the composition on the target site of the skin surface for a sufficient time to remove the undesired skin element and cause the composition to agglomerate into clumps; and rubbing the agglomerated composition so as to remove the agglomerated composition from the skin surface. The agglomerated composition may be removed by various means, such as by use of hands or fingers, or a device such as a wipe or cloth.

The composition may be made by various inventive methods. In one aspect, a method of making the cleansing composition includes the steps of: mixing a first liquid component including an anionic or nonionic surfactant with a first solid component, including a plurality of cellulose particles to form a biphasic composition; and mixing a first gaseous component into the biphasic composition to form a triphasic composition; where the triphasic composition is a substantially homogeneous cleansing composition. In another aspect, the method may include the steps of: mixing a first liquid component including an anionic or nonionic surfactant with a first gaseous component to form a biphasic composition; and mixing a first solid component including a plurality of cellulose particles into the biphasic composition to form a triphasic composition; where the triphasic composition is a substantially homogeneous cleansing composition.

DETAILED DESCRIPTION

The present invention relates to products for cleansing the skin of users, and in particular is directed to products that are considered mild to the skin. The present invention also includes methods of making cleansers and methods of using cleansers. As defined herein, "mildness" refers to compositions that are mild to the skin and/or eyes. As defined herein, a composition that is "mild to the skin" refers to compositions that have low skin irritancy properties as indicated by: a) a relatively high TEP value as determined in accordance with the TEP Test as set forth herein; and/or b) a passing score in the four screening tests (cell viability; cell lysis; and cytokine release (IL-1α and IL-1ra)) performed in accordance with the Skin Assay Test as set forth herein.

As used herein, a composition that is "mild to the eyes" refers to compositions that possess a relatively high TEP value as determined in accordance with the TEP Test as set forth herein. As used herein, a composition that is "substantially free of ocular sting" or "substantial lack of ocular sting" refers to compositions that possess relatively low sting values as determined in accordance with the Ocular Sting Test as set forth herein.

Skin Assay Test—Mildness is determined using a skin equivalent model as described by Bernhofer, et al., Toxicology in Vitro, 219-229 (1999), which is incorporated by reference herein. This model utilizes sequential screens for determining cell viability, cell lysis and cytokine release in order to evaluate the mildness of a surfactant system to the skin. Cell viability is determined using an alamarBlue® assay, which is an indicator of metabolic activity. Cell lysis is detected by measuring lactate dehydrogenase (LDH) activity released from the cytosol of damaged cells. Cytokine release (both IL-1∝ and IL-1ra) is measured for those sample sets which do not exhibit loss of cell viability or cell lysis.

In general, an EpiDerm® Epi-100 human epidermal model is obtained from MatTek Corporation (Ashland, Mass. USA) and maintained according to the manufacturers' instructions. Normal human-derived epidermal keratinocytes (NREK) are then cultured to form a multilayered differentiated model of the epidermis. After a set of NREKs is exposed in triplicate to 100 μl of a topically applied surfactant sample, it is incubated for about 1 hour. After incubation, the set is washed five times, 400 μl per wash, with phosphate buffered saline (PBS), placed onto a fresh assay media, and returned to the incubator for about 24 hours.

Cell viability of the NREKs is determined 24 and 48 hours post treatment with the alamarBlue® assay (Alamar Biosciences. Sacramento. Calif. USA) in accordance with manufacturers' protocols and a Cytofluor II Fluorescent Plate Reader (PerSeptive Biosystems. Framingham. Mass. USA). Cell lysis is determined colorimetrically using an LDH cytotoxicity detection kit (Boehringer-Mannheim). Cytokine content is measured using human calorimetric ELISA kits for IL-1∝ (ENDOGEN. Cambridge, Mass. USA), interleukin-1 receptor antagonist (IL-1ra, R&D Systems. Minneapolis. Minn. USA), granulocyte-macrophage colony stimulating factor (GM-CSF). interleukin-6 (IL-6), interleukin-8 (IL-8). interleukin-IO (IL-b) and TNF∝ (PerSeptive Diagnostics. Cambridge, Mass. USA).

An ocular sting test may be used, in which one (1) drop of a sample (e.g. a 10% dilution of a cleansing composition in water) at a temperature of about 38° C. is instilled into a subject's eye. A new sterile disposable eyedropper is used for each sample and disposed of after being used on only one individual's eye. All instillations are performed either by an investigator or by a trained technician. Within 30 seconds, or as closely as possible following instillation, the subject is asked to grade the perceived stinging sensation to the eye utilizing the following criteria: Sting (0=Within normal limits; 1=Mild, very slight; 2=Moderate; 3=Severe). After 15 minutes and 60 minutes post-instillation, the subject is again asked to grade the perceived stinging sensation to the eye.

A Trans-Epithelial Permeability Test ("TEP Test") may also be used. Irritation to the eyes expected for a given formulation is measured in accordance with the Invittox Protocol Number 86, the "Trans-epithelial Permeability (TEP) Assay" as set forth in Invittox Protocol Number 86 (May 1994). In general, the ocular irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the EC50 (the concentration of test material that causes 50% of maximum dye leakage, i. e., 50% damage to the permeability barrier). Higher scores are indicative of milder formulas.

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

The present invention is specifically directed to a cleansing composition that is suitable for cleansing skin without or with only minimal irritation, and which is suitable for use on sensitive skin, and which may be considered "mild to the skin" as noted above. In one aspect, the cleansing composition may include three distinct phases, therefore being a triphasic composition. The triphasic composition includes at least one solid component, at least one liquid component, and at least one gaseous component mixed and dispersed within the triphasic composition. As described herein, it is not sufficient that the composition merely be exposed to a gaseous material (such as air), but the gaseous material is to be mixed or interspersed into and throughout the resulting triphasic composition. The triphasic compositions described herein are suitable for cleansing skin effectively and safely.

The cleansers described herein are useful in removing undesired elements from the skin of the user, such elements being anything to be removed from the skin, including, for example, dirt, oil, makeup, and potentially harmful bacteria. As will be described below, the cleansing compositions herein are capable of removing at least 90% of makeup from the skin of the user after application and limited rubbing, or at least 95% of makeup from the skin of the user after application and limited rubbing, or at least 99% of makeup from the skin of the user after application and limited rubbing. For example, after application of the cleanser onto the skin surface intended to be treated, the cleanser may be rubbed onto the target skin surface for about five revolutions with a finger or other cleaning device or tool, such as a pad, wipe, cloth, or other suitable device. In some aspects, the cleanser may be rubbed for about 10 revolutions. A method of using the triphasic cleanser is also included, in which a user rubs the triphasic cleanser on the skin for a sufficient length of time to cause the triphasic cleanser to remove undesirable skin elements (defined below), while the cleanser agglomerates and is pushed off or falls off of the skin surface. This method may be achieved without the use of added water (beyond any water in the cleansing composition) or may include added water, either during or after application of the triphasic cleanser to the skin.

The present invention is useful in removing undesirable elements (as noted above, for example, dirt, oil, makeup, and bacteria) from the skin of the user without requiring the use of added water or washing with water. Of course, a user may choose to rinse or wash the skin with water, but in preferred aspects, the present invention provides composition for and a method of cleansing the skin without using added water to aid in cleansing the skin. For example, after use, skin may be treated by rubbing or wiping with a dry cloth or other water-free aid. Through the present invention, the cleanser is capable of removing such undesirable elements by rubbing on the skin with a hand or fingers, or with a cleaning device or tool such as a wipe, pad, or other cloth, and without added water during or after use. During use, such as after the cleanser is applied and the user begins to rub the cleanser onto the surface of the skin, the cleanser begins to solidify in clumps or agglomerates, and the clumps or agglomerates begin to fall off of the skin through rubbing (or they are pushed off the skin by a user's hand or such a cleaning device or tool described above). These clumps or agglomerates eventually fall off the skin after having cleansed the skin. Therefore, the present invention is particularly useful in cleansing skin of users without the need for significant water or bathing. Further, after the skin is cleansed, there is no need to wash or rinse the skin to remove a majority of cleanser material that may be left on the skin as in traditional cleansers. While there may be trace amounts of the triphasic material left on the skin after use, the amount remaining on the skin is less than about 5% of the cleansing composition that was originally applied to the skin surface prior to rubbing on the skin surface. Thus, rinsing after use is not required.

The cleansers described herein are suitably mild and are capable for cleansing sensitive skin, including skin of babies or toddlers, as well as adult skin. The cleansers herein may be useful in cleansing skin of babies, such as babies suffering from cradle cap.

As noted above, the cleanser may be a triphasic cleanser, including a solid component, a liquid component and a gaseous component.

It is desirable that the cleansing products described herein include at least one solid component that is mild to the skin of a user and provides a desired feel and/or abrasive effect. In one aspect, the solid component may include or consist of a plurality of cellulose particles. It is particularly preferred that such cellulosic materials consist of cotton or consist essentially of cotton, as will be described below, to maintain a low risk of irritation and rash.

The cellulosic materials are particulate, and may be spherical or may be linear particles, or combinations thereof. As used herein, the term "linear particle" means a particle having one dimension ("length") that is greater than another dimension (e.g., "diameter" or "width"). Linear particles may be measured and defined by size by subjecting such particles to analysis with respect to a series of sieves having different mesh sizes. Generally, a sample of linear particles may have a distribution of particle sizes throughout the sample. Thus, linear particle sizes as expressed herein are expressed as an average particle size and reflect the average length of the particles contained within the sample.

Preferably, the average size of linear particles useful in the compositions and methods of this invention is less than about 1000 μm in length, or less than about 600 μm in length, or less than about 500 μm in length, or in some aspects, the average length ranges from about 50 to about 700 μm, or from about 300 to about 600 μm. In some instances, the width or diameter of linear particles useful in the compositions and methods of this invention may be about 1 to about 100 μm, or from about 2 to about 50 μm in width or diameter, or about 20 to about 40 μm in width or diameter. It is understood that a plurality of cellulose particles may include some particles that have smaller and/or longer lengths or widths, due to the nature of forming the particles, but the desired size (length or width) described above is for an average particle in the composition.

As used herein, the term "particle aspect ratio" means the ratio of the length of a particle to its width or diameter. Preferably, the particle aspect ratio of linear particles useful in the compositions and methods of this invention is from about 2 to about 20. More preferably, the particle aspect ratio is from about 2 to about 15 and most preferably, from about 2 to about 10. The aspect ratio of spherical particles is about 1 to 1. The particulate compositions used herein may include a plurality of linear particles and spherical particles in combination, if desired.

As used herein, the term "cellulose" refers to a polysaccharide material consisting of long unbranched chains of linked glucose units. Cellulose materials useful in the compositions and methods of this invention may be derived from cotton, corn, wood pulp, bamboo pulp, silk, cork and the like. Preferably, the cellulose materials useful in the compositions of this invention are derived from cotton. The cellulosic particles may be from fibers recovered from post-industrial scrap or may be derived from raw cotton. Scrap is derived from waste or other pre-consumer cotton products from, for example, the apparel, carpet, furniture and household goods industries. Synthetic or regenerated cotton or cellulose materials may also be used as sources for the cellulose particles useful in the compositions and methods of this invention, including rayon, viscose, cellophane, and other cellulosic materials with a substantially uniform and reproducible molecular size and distribution.

The cellulose materials useful in the compositions and methods of this invention may be derived directly from the source plant (referred to herein as, "raw" or virgin particles) or may be generated from cloth or nonwoven materials previously formed from plant or cellulose fibers (referred to herein as "regenerated" particles). For example, cotton cloth may be processed so as to break the cloth into small particles and/or uniform fiber length by cutting the length of the cotton fibers from inches to microns. This random-cut fiber is available in several grades, white, dark, and unbleached, with average fiber lengths described above. The cellulose particles used herein may be linear, spherical, or a combination of linear and spherical particles, and may be prepared from regenerated cotton or raw cotton.

Typical mechanical milling processes such as those useful in cutting down the size of the cellulose materials useful in the compositions and methods of this invention, for example, are described in U.S. Pat. No. 7,594,619 and U.S. Pat. No. 6,656,487, which are hereby incorporated herein by reference.

Generally, the cellulose particles useful in the compositions of this invention may be processed according to the any known methods. One such method comprises mixing a cellulosic material derived from scrap, as defined above, with at least one of grinding aids selected from the group including water, fatty acids, synthetic polymers and organic solvents, and, after mixing, mechanically grinding the mixture.

Another method of obtaining cellulose particles is freezing a cellulosic material derived from post-industrial scrap at a low temperature, and then mechanically grinding the frozen material. Cellulose particles useful herein may be hydrophobic or may be hydrophilic.

The cellulose particles useful in the compositions and methods of this invention may be further treated with hydrophobic agent(s) to yield more hydrophobic cellulose particles. For example, a hydrophobic coating agent may be used to treat the cellulose particles. The hydrophobic coating agent may be any such agent known to one of skill in the art. Preferred hydrophobic coating agents react chemically with the cellulose particles to provide a durable covalent bond thereto and have hydrophobic chemical backbones or substituents that can provide a hydrophobic outer layer around each individual cellulose particle. The coating agent may react, for example, with hydroxyl groups, available oxygen atoms present on the surface of the cellulose particle being coated. Coatings may be applied prior to or after milling the cellulose particles.

Hydrophobic agents may include, but not limited to, low water soluble organic compounds such as metal soap, e.g., a metal myristate, metal stearate, a metal palmitate, a metal laurate or other fatty acid derivatives known to one of skill in the art. Other hydrophobic agents may include an organic wax, such as a synthetic wax like polyethylene or a natural wax like carnauba wax. Hydrophobic agents useful in coating the cellulose particles useful in the compositions and methods of this invention may also be long chain fatty acids or esters such as stearic acid, oleic acid, castor oil, isododecane, silicone, and their derivatives, non-water soluble polymers, e.g. high molecular weight methylcellulose and ethylcellulose, and high molecular water insoluble fluoropolymers etc., polymerized siloxanes or polysiloxanes with the chemical formula [R2SiO]n, where R is an organic group such as methyl, ethyl, or phenyl, such as dimethicone, dimethicone copolyol, dimethicone ester; methicone and their derivatives. Examples of hydrophobic linear cotton particles useful in the present invention include, but are not limited to, Cotton Fiber Flock CD60 available from Goonvean Fiber and W200 and W325 White Cotton Flock available from International Fiber Corporation.

The use of the cellulose particles described herein is effective in providing a gentle abrasive material in the cleanser. Cellulose particles, particularly those derived from cotton and having the sizes and characteristics described above, are sufficiently mild, and therefore are less likely to cause significant irritation to the skin of the user than the use of other abrasive agents such as beads, but cellulose particles are effective in increasing the removal of undesirable skin elements. The cellulose particles may be included in the cleansing compositions in the amount of about 2-60% (w/w), more preferably about 10-40% (w/w), and most preferably about 15-25% (w/w). The cellulose particles are desirably added to a cleansing composition and thoroughly dispersed throughout that composition to provide a substantially uniform cleansing composition.

It has been found that while the inclusion of cellulose particles into a cleanser is effective, including cellulose particles as part of a triphasic cleanser is even more effective. Desirably, the compositions described herein include at least three different phase materials expressly included into and forming the composition, including a solid component, a liquid component and a gaseous component. The cellulose particles may be used to form the solid phase material. A suitable cleansing liquid may serve as a liquid phase material, and a gas, such as air, forms a gaseous phase material. As noted above, it is not sufficient that the composition merely be exposed to air, but air must be mixed in and embedded into the cleansing composition to a desired amount to provide a triphasic composition described herein. For example, the triphasic composition may include about 5% to about 40% gaseous material (by volume), or more desirably about 10-20% by volume gaseous material.

In certain embodiments, the triphasic composition is a flowable composition including a greater amount (by volume) of liquid phase material(s) than solid phase material, and in other embodiments, the triphasic composition may have more of a slurry or paste type composition, including a greater volume of solid materials, or including solid materials having a larger size or aspect ratio. In some aspects, the volumetric ratio of solid materials to liquid materials in the composition may be approximately equal. The ratio of liquid to solid materials in the final composition may vary depending upon the final texture and feel desired. The greater the amount of liquid materials as compared to solid materials, the more flowable the composition may be, and vice versa.

The triphasic composition includes at least one cleansing liquid component. In preferred embodiments, the liquid component includes at least one cleansing liquid selected from the group consisting of saponified fat, anionic surfactant, and nonionic surfactant. In some embodiments, the composition may be substantially free of any surfactants, or it may be substantially free of cationic surfactants. "Substantially free", as used herein, means less than 0.1% of the resulting triphasic composition includes the component (e.g., a surfactant, or a cationic surfactant, respectively). In desired embodiments, "substantially free" of any surfactant means that there is no added surfactant in the final composition, and "substantially free" of any cationic surfactant means that there is no added cationic surfactant in the final composition.

If used, a saponified fat may include, for example, saponified triglyceride, or other fat desired. If used, the term "nonionic surfactant" means an amphiphilic molecule comprising one or more nonionic hydrophilic and/or hydrophobic moieties. Nonionic Surfactants do not ionize in aqueous solution, because the hydrophilic moieties are nondissociable, such as alcohol, phenol, ether, ester, or amide. Examples of hydrophilic nonionic surfactants include, but are not limited to, polyethoxylated and glucoside (sugar based) nonionics. Examples of hydrophobic nonionic surfactants are often of alkyl (of fatty acids of natural origin) or alkylbenzene based. Other examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyethyleneoxy derivatives of polyol esters, wherein the polyethyleneoxy derivative of polyol ester (1) is derived from (a) a fatty acid containing from about 8 to about 22, and preferably from about 10 to about 14 carbon atoms, and (b) a polyol selected from sorbitol, sorbitan, glucose, .alpha.-methyl glucoside, polyglucose having an average of about 1 to about 3 glucose residues per molecule, glycerine, pentaerythritol and mixtures thereof, (2) contains an average of from about 10 to about 120, and preferably about 20 to about 80 ethyleneoxy units; and (3) has an average of about 1 to about 3 fatty acid residues per mole of polyethyleneoxy derivative of polyol ester. Examples of such preferred polyethyleneoxy derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from Croda, Inc. of Edison, N.J. under the tradename, "Atlas G-4280." Polysorbate 20, which is the laurate monoester of a mixture of sorbitol and sorbitol anhydrides condensed with approximately 20 moles of ethylene oxide, is available commercially from Croda, Inc. of Edison, N.J. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl glucosides comprise from about 1 to about 6 glucose residues per molecule of alkyl glucoside. A preferred glucoside is decyl glucoside, which is the condensation product of decyl alcohol with a glucose polymer and is available commercially from Cognis Corporation of Ambler, Pa. under the trade name, "Plantaren 2000." Additional examples of nonionic surfactants can be found in U.S. Pat. No. 8,399,590 incorporated herein by reference.

If used, "anionic surfactants' means molecules bearing a negative charge which are dissociated in water in an amphiphilic anion*, and a cation*, such as an alkaline metal (Na+, K+) or a quaternary ammonium. Examples of anionic surfactants include, but not limited to, alkylbenzene sulfonates, lauryl sulfates, di-alkyl sulfosuccinates, and lignosulfonates.

Examples of certain anionic surfactants include structures described in U.S. Pat. No. 8,258,250, the contents of which are incorporated herein by reference, and which describe the structures for anionic surfactants such as: alkyl sulfates; alkyl ether sulfates; alkyl monoglyceryl ether sulfates; alkyl monoglyceride sulfates; alkyl monoglyceride sulfonates; alkyl sulfonates; alkylaryl sulfonates; alkyl sulfosuccinates; alkyl ether sulfosuccinates; alkyl sulfosuccinamates; alkyl amidosulfosuccinates; alkyl carboxylates; alkyl amidoethercarboxylates; alkyl succinates; fatty acyl sarcosinates; fatty acyl amino acids; fatty acyl taurates; and fatty alkyl sulfoacetates; alkyl phosphates, and mixtures and combinations thereof. Additional examples of anionic surfactants can be found in U.S. Pat. No. 8,399,590 incorporated herein by reference.

The triphasic composition also includes a gaseous material mixed or embedded within the composition, such as air. For example, ambient air may be introduced into the triphasic composition through vigorous mixing, which causes aeration of the batch. The formulation is desirably formulated such that the solid and/or liquid components in the composition effectively suspend the gaseous material, and where mechanical energy is required to effectively de-aerate the gas-containing composition. As will be described below, in some instances it is beneficial to combine solid and liquid components to arrive at a biphasic composition, and then introduce air or other gaseous material into the biphasic composition, thereby forming a triphasic composition. In other aspects, it may be beneficial to introduce air or gaseous material into the liquid material(s) first, to form an aerated liquid composition, and then add solid component(s) to this aerated liquid composition to form a triphasic composition. It has been discovered by the present applicant that the presence of the cellulosic particles described above within a liquid composition allows for effective and sustained gas embedding within the composition, forming a stable and useful triphasic composition that requires mechanical force to deaerated the triphasic composition.

Biocompatible gases used to prepare the present invention include, but are not limited to, air, nitrogen, oxygen, carbon dioxide and other such gases. The gases can be mixed with solid and/or liquid phases (or with a biphasic composition including solid and liquid phases) to form a triphasic composition. It is preferred that the resulting triphasic composition have a substantially homogeneous dispersion of the three phases. Complete homogeneity is not expected, however, substantial homogeneity is desired. Upon formation of the triphasic composition, the dispersion of the gas phase provides the composition with the improved physical properties such as flowability, extrudability and injectibility as well as enhanced cleansing efficacy.

Finally, it is desirable that the triphasic composition includes a cosmetically acceptable carrier and may include other components commonly incorporated and used in cleansers.

The compositions of the present invention may comprise any of a variety of additional other ingredients used conventionally in healthcare/personal care compositions (referred to generally as "personal care components"). These other personal care components nonexclusively include one or more, pearlescent or opacifying agents, thickening agents, emollients, secondary conditioners, humectants, chelating agents, actives, exfoliants, and additives which enhance the appearance, feel and fragrance of the compositions, such as colorants, fragrances, preservatives, pH adjusting agents, and the like.

Any of a variety of commercially available pearlescent or opacifying agents which are capable of suspending water insoluble additives such as silicones and/or which tend to indicate to consumers that the resultant product is a conditioning shampoo are suitable for use in this invention. If used, the pearlescent or opacifying agent may be present in an amount, based upon the total weight of the composition, of from about 0.1 percent to about 10 percent, e.g. from about 1.5 percent to about 7 percent or from about 2 percent to about 5 percent. Examples of suitable pearlescent or opacifying agents include, but are not limited to mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: $HO-(JO)_a-H$, wherein J is an alkylene group having from about 2 to about 3 carbon atoms; and a is 2 or 3; fatty alcohols containing from about 16 to about 22 carbon atoms; fatty esters of the formula: $KCOOCH_2L$, wherein K and L independently contain from about 15 to about 21 carbon atoms; inorganic solids insoluble in the shampoo composition, and mixtures thereof.

The pearlescent or opacifying agent may be introduced to the mild cleansing composition as a pre-formed, stabilized aqueous dispersion, such as that commercially available from Cognis Corporation of Ambler, Pa. under the tradename, "Euperlan PK-3000." This material is a combination of glycol distearate (the diester of ethylene glycol and stearic acid), Laureth-4 $(CH_3(CH_2)_{10}CH_2(OCH_2CH_2)_4OH)$ and cocamidopropyl betaine.

Compositions useful in the present invention may also include any of a variety of conventional thickeners that do not meet the requirements specified above in order to be considered micellar thickeners. Examples of suitable conventional thickeners include various thickeners having molecular weights of greater than about 100,000 grams per mole, including chemistries such as: hydroxyalkyl cellulose; alkyl cellulose; hydroxyalkyl alkyl cellulose; xanthan and guar gums, succinoglycan gums; and mixtures thereof.

Examples of suitable thickening agents nonexclusively include: mono or diesters of 1) polyethylene glycol of formula: $HO-(CH_2CH_2O)_zH$, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; hydrophobically-modified alkali swellable emulsions (HASEs); hydrophobically-modified ethoxylated urethanes (HEURs); xanthan and guar gums; and mixtures thereof. Thickeners include polyethylene glycol ester, such as PEG-150 distearate which is available from the Hallstar Company of Chicago, Ill. under the tradename, "PEG 6000 DS".

Any of a variety of commercially available secondary conditioners, such as volatile silicones, which impart additional attributes, such as gloss to the hair are suitable for use in this invention. The volatile silicone conditioning agent has an atmospheric pressure boiling point less than about 220 C. The volatile silicone conditioner may be present in the invention, in ranges of from about 0 percent (if unused) to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, such as cyclomethicone fluids. Other suitable secondary conditioners include cationic polymers, including polyquarterniums, cationic guar, and the like. The present inventive compositions may be free of added silicones.

Any of a variety of commercially available humectants, which are capable of providing moisturization and conditioning properties to the personal cleansing composition, are suitable for use in the present invention. The humectant may be present in an amount of from about 0 percent (if unused) to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, polyglycerols, and mixtures thereof; 2) polyalkylene glycol of the formula: $HO-(R''O)_b-H$, wherein R" is an alkylene group having from about 2 to about 3 carbon atoms and b is an integer of from about 2 to about 10; 3) polyethylene glycol ether of methyl glucose of formula $CH_3-C_6H_{10}O_5-(OCH_2CH_2)_c-OH$, wherein c is an integer from about 5 to about 25; 4) urea; and 5) mixtures thereof.

Examples of suitable chelating agents include those which are capable of protecting and preserving the compositions of this invention. The chelating agent may include ethylenediamine tetracetic acid ("EDTA"), such as tetrasodium EDTA, available commercially from Dow Chemical Company of Midland, Mich. under the tradename, "Versene 100XL" and is present in an amount, based upon the total weight of the composition, from about 0 (if unused) to about 0.5 percent or from about 0.05 percent to about 0.25 percent.

Suitable preservatives include, for example, parabens, quaternary ammonium species, phenoxyethanol, benzoates, DMDM hydantoin, and are present in the composition in an amount, based upon the total weight of the composition, from about 0 (if unused) to about 1 percent or from about 0.05 percent to about 0.5 percent.

In one embodiment, the composition comprises a first liquid component, a first solid component, and a first gaseous component, each described herein, and also includes a carrier, preferably a cosmetically-acceptable carrier. As used herein, the term "cosmetically-acceptable carrier" means a carrier that is suitable for use in contact with the skin without undue toxicity, incompatibility, instability, irritation, allergic response, and the like. The compositions can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: polyglycerols, propylene glycol, polyethylene glycol (200, 600), polypropylene glycol (425, 2025), glycerol, 1,2,4-butanetriol, sorbitol esters, 1,2,6-hexanetriol, ethanol, and mixtures thereof.

According to certain embodiments, compositions useful in the subject invention may be formulated as a solution comprising an emollient. As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32 43 (1972) and the International Cosmetic Ingredient Dictionary and Handbook, eds. Wenninger and McEwen, pp. 1656 61, 1626, and 1654 55 (The Cosmetic, Toiletry, and Fragrance Assoc., Washington, D.C., 7.sup.th Edition, 1997) (hereinafter "ICI Handbook") contains numerous examples of suitable materials. A lotion can be made from such a solution. Lotions typically comprise from about 1% to about 20% (e.g., from about 5% to about 10%) of an emollient(s) and from about 50% to about 90% (e.g., from about 60% to about 80%) of water.

In certain embodiments, the compositions produced via the present invention are preferably used as or in personal care products for treating or cleansing at least a portion of a human body. Examples of certain personal care products include various products suitable for application to the skin, hair, oral and/or perineal region of the body, such as shampoos, hand, face, and/or body washes, bath additives, gels, lotions, creams, and the like. As discussed above, applicants have discovered unexpectedly that the instant methods provide personal care products having reduced irritation to the skin and/or eyes and, in certain embodiments one or more of desirable properties such as flash foaming characteristics, rheology, and functionality, even at high surfactant concentrations. Such products may further include a substrate onto which a composition is applied for use on the body. Examples of suitable substrates include a wipe, pouf, sponge, and the like as well as absorbent articles, such as a bandage, sanitary napkin, tampon, and the like.

The present invention provides methods of treating and/or cleansing the human body comprising contacting at least a portion of the body with a composition of the present invention. Certain methods comprising contacting mammalian skin, hair and/or vaginal region with a composition of the present invention to cleanse such region and/or treat such region for any of a variety of conditions including, but not limited to, acne, wrinkles, dermatitis, dryness, muscle pain, itch, and the like. Any of a variety of actives or benefit agents known in the art for treating such conditions may be used in the present invention.

What is meant by a "benefit agent" is an element, an ion, a compound (e.g., a synthetic compound or a compound isolated from a natural source) or other chemical moiety in solid (e.g. particulate), liquid, or gaseous state and compound that has a cosmetic or therapeutic effect on the skin.

The compositions of the present invention may further include one or more benefit agents or pharmaceutically-acceptable salts and/or esters thereof, the benefit agents generally capable of interacting with the skin to provide a benefit thereto. As used herein, the term "benefit agent" includes any active ingredient that is to be delivered into and/or onto the skin at a desired location, such as a cosmetic or pharmaceutical.

The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed.

Examples of suitable benefit agents include those that provide benefits to the skin, such as, but not limited to, depigmentation agents; reflectants; amino acids and their derivatives; antimicrobial agents; allergy inhibitors; anti-acne agents; anti-aging agents; anti-wrinkling agents, antiseptics; analgesics; shine-control agents; antipruritics; local anesthetics; anti-hair loss agents; hair growth promoting agents; hair growth inhibitor agents, antihistamines; anti-infectives; anti-inflammatory agents; anticholinergics; vasoconstrictors; vasodilators; wound healing promoters; peptides, polypeptides and proteins; deodorants and anti-perspirants; medicament agents; skin firming agents, vitamins; skin lightening agents; skin darkening agents; antifungals; depilating agents; counterirritants; hemorrhoidals; insecticides; enzymes for exfoliation or other functional benefits; enzyme inhibitors; poison ivy products; poison oak products; burn products; anti-diaper rash agents; prickly heat agents; vitamins; herbal extracts; vitamin A and its derivatives; flavonoids; sensates; anti-oxidants; hair lighteners; sunscreens; anti-edema agents, neo-collagen enhancers, film-forming polymers, chelating agents; anti-dandruff/sebhorreic dermatitis/psoriasis agents; keratolytics; and mixtures thereof.

The cleansing methods of the present invention may further comprise any of a variety of additional, optional steps associated conventionally with cleansing hair and skin including, for example, lathering, rinsing steps, and the like. As discussed above, however, it is desired that the method of use does not require rinsing with added water, and may simply require rubbing the skin with the user's hand or fingers, or with a dry cloth or other water-free article. Thus, in these embodiments, after the product has been applied and rubbed sufficiently to cleanse the skin to a desired level, the product remaining on the skin surface is caused to agglomerate and, in fact, does agglomerate during the step of rubbing on the skin, and is capable of being substantially removed by rubbing or brushing the skin without added cleansing agents, including water.

The present invention also includes a method for making a triphasic composition, such that the resulting composition is stable and effective in cleansing a skin. In a process for making the stable triphasic composition, a first volume of a cleansing liquid is mixed with a second volume of a gas under conditions effective to mix the liquid and the gas together to form a stable two-phase composition. The liquid/gas composition desirably comprises a discontinuous gas phase comprising the gas dispersed throughout a continuous cleansing liquid phase comprising at least one cleansing liquid. The cleansing liquid may include other carriers and optional components described above. In preferred embodiments, the cleansing liquid includes a saponified fat or surfactant, and the gas includes air. An amount of solid hydrophobic, linear cellulose particles, which may be at least partially insoluble in the cleansing liquid, is introduced into the two-phasic composition, and mixed together under conditions effective to form a substantially homogenous triphasic composition comprising the discontinuous gas phase and the solid particles substantially uniformly or homogenously dispersed throughout the continuous liquid phase.

In an alternative method, the first volume of a cleansing liquid is mixed with a first solid component, which may include an amount of solid, hydrophobic linear cellulose particles. The liquid and solid components may be mixed together to form a substantially homogeneous biphasic composition. To this biphasic composition is dispersed a gaseous component, as described above. The three components are mixed together under conditions effective to form a substantially homogenous triphasic composition comprising the discontinuous gas phase and the solid particles substantially uniformly or homogenously dispersed throughout the continuous liquid phase. As also noted above, the presence of the hydrophobic cellulose particles within the liquid phase allows for effective sustaining and trapping of gas within the triphasic composition, giving the composition a longer shelf life and sustainability.

The respective volumetric ratios of the cleansing liquid, the gas and the solid hydrophobic, linear cellulose particles may vary to provide the desired resulting triphasic composition. It is particularly desirable to include a sufficient amount of each component to provide the resulting triphasic skin care composition with effective cleansing properties, yet maintains its mildness and stability. In some embodiments using a substantially similar amount of liquid and solid components, the gaseous material may be added in any desired amount. For example, if the solid and liquid materials are present in about the same amount, the cleansing liquid, gas, and solid component may be present at ratios of from about 1:2:1 to about 1:20:1 based on volume: volume :weight (ml:ml:g), respectively; or from about 1:4:1 to about 1:10:1, based on volume: volume :weight (ml:ml:g), and more preferably from about 1:6:1 to about 1:8:1, based on volume: volume :weight (ml:ml:g). The amount of the liquid and solid components may be modified with respect to each other as well, as described above, and may be present in ratios of from about 20:1 (liquid to solid components) to about 1:20 (liquid to solid components) (ml:g). The volumetric amount of the gaseous element may be modified depending upon the level and amount of liquid and/or solid components in the composition. The resulting triphasic composition may be thick, such as a slurry or a paste, or it may be a little more flowable, such as a gel or lotion-like cleanser, or it may be most flowable, having a more liquid consistency, as described above by modifying the amount of liquid component(s) relative to the solid component(s).

Depending on the type and amount of liquid materials used with respect to the solid materials used, and the desired resulting flowability of the triphasic composition, formulations described herein may have viscosities between about 1,000 to about 1,000,000 cps (measured at room temperature) for a thick, paste-like composition, or a slightly flowable cream-like composition, or the most flowable gel-like compositions of the present invention. For example, the present invention may include compositions having viscosities of between about 150,000 to about 1,000,000 cps at room temperature for thick, paste-like compositions (least flowable), or viscosities between about 30,000 to about 150,000 cps at room temperature for cream-like (slightly flowable) compositions, or viscosities between about 1,000 to about 30,000 cps at room temperature for more gel-like (most flowable) compositions of the present invention.

The liquid phase, the solid phase and the gaseous phase are present in relative amounts effective to provide a desired feel and viscosity. Upon formation of the composition by dispersion of the particles in the slurry/paste, the dispersion of the gas phase in the composition provides the composition with improved physical properties relating to flowability, extrudability and injectability.

The present invention includes a packaged product including a triphasic composition in a pre-mixed state. The package may include a means for dispensing the product, such as a pump, or it may be opened by a user and a desired amount of the triphasic product removed by hand or with a cleaning device or tool. The product may be contained in a package including at least two phases maintained separately, and include a pump or other means to mix the phases prior to use by a user. For example, the product may include the solid and liquid materials in a biphasic composition, with an aerating pump that causes aeration during dispensing by a user. In other embodiments, the product is provided to a user and dispensed by the user in a stable, triphasic form.

In use, the product is used by the user in a state wherein the three phase materials described above are mixed to a substantially uniform or homogenous triphasic state. The mixing may be performed prior to the user handling the product or the user may mix the components prior to use. A desirable amount of the triphasic cleanser material is dispensed or retrieved by a user and placed onto the surface of the skin in which cleansing is desired. The composition is rubbed onto the desired target surface of the skin by the user, either by rubbing with fingers or a hand, or by rubbing with a cleaning device or tool such as a wipe, pad, cloth, cotton ball, or other device. The composition is rubbed for a sufficient time to allow the undesirable skin element (such as dirt, bacteria, makeup, as described above) to be cleaned by the cleansing composition and to also cause the cleansing composition to agglomerate on the surface of the skin and fall or be pushed off of the skin of the user. After the skin has been cleansed, the user may brush or wipe off the target skin with a cloth to remove any remaining product, and in desired embodiments, the further step of brushing or wiping off the skin is achieved in the absence of added water or with wetted materials or cloth. In some aspects, once the composition has agglomerated into solid clumps and fallen off or been pushed off the skin of the user, no further cleansing or washing is required. In some embodiments, the composition may begin to agglomerate and fall off the skin after about 5 to about 10 to about 20 revolutions on the skin.

EXAMPLES

Example 1

Cleansing Efficacy

Four samples were prepared, three describing various inventive embodiments and one that was a comparative example. These samples were tested on a human skin subject. The three inventive samples were either non-ionic (A and B) or anionic (C), and one comparative example (D) was cationic. The cellulose particles for each of the examples were regenerated cotton powder W325J (from IFC, white cotton flock), having an average particle size of 44.04 microns in diameter and 80.20 microns in length.

Inventive Composition A, Non-Ionic

Inventive Composition A (non-ionic) is set forth in the table below, with each component in weight percent, with method of manufacture described below:

| INCI Name | Inventive Example A (non-ionic surfactant) % w/w |
|---|---|
| Water | 62.13 |
| Acrylates/C10-30 Alkyl Acrylate Crosspolymer | 0.50 |
| Glycerin | 0.84 |
| Cocamidopropyl Betaine | 5.88 |
| Coco-Glucoside; Glyceryl Oleate | 0.84 |
| Polyglyceryl-10 Laurate | 0.84 |
| Decyl Glucoside | 11.76 |
| Phenoxyethanol; Ethylhexylglycerin | 0.76 |
| Fragrance | 0.03 |
| Sodium Benzoate | 0.42 |
| Cellulose particles | 16.00 |
| | 100.00 |

Inventive Sample A was prepared by the following procedure: Added water to a beaker, and began mixing. Added Acrylates/C10-30 Alkyl Acrylate Crosspolymer and mixed until completely solubilized. Added sodium benzoate, and mixed until completely dispersed. Began heating to 75-80 C while mixing. Added decyl glucoside and mixed until completely dispersed. Added polyglyceryl-10 laurate, and mixed until completely dispersed. Began cooling to room temperature. Added cocamidopropyl betaine and mixed until homogenous. Added Coco-Glucoside; Glyceryl Oleate and mixed until homogenous. Added glycerin and mixed until homogenous. Added fragrance and mixed until homogenous. Added cellulose particles and continued mixing until fully dispersed.

Inventive Composition B, Non-Ionic

Inventive Composition B (non-ionic) is set forth in the table below, with each component in weight percent, with method of manufacture described below:

| INCI Name | Inventive Example B (non-ionic surfactant) % w/w |
|---|---|
| Water | 72.11 |
| Carbomer | 0.22 |
| Glycerin | 8.40 |
| Cetearyl Alcohol (and) Cetearyl glucoside | 1.51 |
| Polyglyceryl-10 Laurate | 0.84 |
| Phenoxyethanol; Ethylhexylglycerin | 0.67 |
| Caprylyl Glycol | 0.25 |
| Cellulose Particles | 16.00 |
| | 100.00 |

Inventive Sample B was prepared by the following procedure: Added water to a beaker, and began mixing. Added carbomer and mixed until completely solubilized. Began heating to 75-80 C while mixing. At 75 C, added Cetearyl Alcohol (and) Cetearyl glucoside to batch, and mixed until completely homogenous. Began cooling to 35 C. Added Polyglyceryl-10 Laurate and mixed until completely dispersed, while cooling. Once the temperature was below 40 C, added Phenoxyethanol, Ethylhexyglycerin Caprylyl Glycol and mixed until homogenous. Neutralized carbomer with sodium hydroxide to pH of 5.5-6.5. Added cellulose particles and continued mixing until fully dispersed.

Inventive Composition C, Anionic

Inventive Composition C (anionic) is set forth in the table below, with each component in weight percent, with method of manufacture described below:

| INCI Name | Inventive Example C (anionic surfactant) % w/w |
|---|---|
| Water | 66.90 |
| PEG-150 Distearate | 1.22 |
| Glycerin | 0.42 |
| Cocamidopropyl Betaine | 7.06 |
| Sodium Trideceth Sulfate | 3.11 |
| PEG-80 Sorbitan Laurate | 3.74 |
| Phenoxyethanol; Ethylhexylglycerin | 0.59 |
| Fragrance B | 0.15 |
| Polyquaternium-10 | 0.12 |
| Sodium Benzoate | 0.25 |
| Cellulose Particles | 16.00 |
| Tetrasodium EDTA | 0.44 |
| | 100.00 |

Inventive Sample C was prepared by the following procedure: Added water to a beaker, and began mixing while heating to 80-85 C. Added glycerin and continued mixing until fully dispersed. Premixed Polyquaternium-10 with 0.7% water, and mixed until homogenous. Held for addition to main batch. While heating, added 3% of PEG-150 Distearate to the main tank, and continued mixing until fully dispersed. Slowly added the remaining PEG-150 Distearate. When the batch reached 80-85 C, mixed until homogenous. When batch was homogenous, began cooling to room temperature. Added sodium benzoate and continued mixing. Added sodium trideceth sulfate and continued mixing. Added cocamidopropyl betaine and continued mixing. Premixed fragrance with 1.0% PEG-80 sorbitan laurate and mixed until homogenous. Below 40 C, added phenoxyethanol, ethylhexylglycerin, Tetrasodium EDTA and fragrance premix, and continued mixing. Added remaining PEG-80 sorbitan laurate and continued mixing. Adjusted pH to 5.0-5.5 using citric acid and/or sodium hydroxide. Added cellulose particles and continued mixing until fully dispersed.

Comparative Composition D, Cationic

Comparative Composition D (cationic) is set forth in the table below, with each component in weight percent, with method of manufacture described below:

| INCI Name | Comparative Example D (cationic surfactant) % w/w |
|---|---|
| Water | 59.34 |
| Glycerin | 10.08 |
| Distearyldimonium Chloride | 4.20 |
| Cetyl Alcohol | 2.10 |
| Benzyl Alcohol | 0.50 |
| Petrolatum | 3.36 |
| Dimethicone | 1.05 |
| Isopropyl Palmitate | 2.52 |
| Sodium Chloride | 0.01 |
| Cellulose Particles | 16.00 |
| Avena Sativa (Oat) Kernel Oil | 0.84 |
| | 100.00 |

Comparative Sample D was prepared by the following procedure: Added water to a beaker, and began mixing while heating to 80-85 C. Above 70 C, added oatmeal and sodium chloride to the batch and continued mixing. Added distearyldimonium chloride and continued mixing until homogenous. At 80-85 C, added cetyl alcohol and continued mixing until fully dispersed. Began cooling to room temperature. While mixing and cooling, added dimethicone, petrolatum and isopropyl palmitate. Added glycerin and continued mixing. Below 50 C, added benzyl alcohol and continued mixing. Added cellulose particles and continued mixing until fully dispersed.

Method of Assessing Efficacy

On the skin of a human subject's arm, the four samples described above were applied and tested for assessing cleansing efficacy. First, the test area of the skin was covered with waterproof eye make-up (black shade) and allowed to dry for 10 minutes. Four test areas were used on the same skin of the human subject concurrently. After the test area was dried, about 0.1 cc of sample cleanser was applied to each of the designated test sites. Compositions A-D above were each individually applied to each of the test sites. Each test area was covered with the designated Composition using the contralateral index finger for five revolutions. Observations were recorded. An additional five revolutions on each test site were completed using the contralateral index finger. Observations were again recorded.

Results were obtained through visual examination of each site after five and ten revolutions, respectively. The visual observation compared the amount of makeup remaining on the skin surface after the cleanser had been rubbed for the 5 and 10 revolutions, respectively.

Photographs were taken of the sample arm to show the four products that were evaluated, and the photographs are shown in FIG. 1. FIG. 1 shows, from left to right: pre-application after the waterproof eye makeup was applied; after application of the sample cleansing product; after five revolutions with fingers; and after 10 revolutions with fingers. The Inventive Example A is seen as the upper-left sample (depicted by the negative indicator on the arm). Inventive Example B is the middle sample. Inventive Example C is the upper-right sample on the arm (depicted by the letter "C" on the arm). Comparative D is the bottom right sample on the arm (depicted by the plus sign on the arm).

Inventive Example A (non-ionic) was deemed to have the best cleansing efficacy, as determined by visual evaluation. Inventive Example B (non-ionic) was second best, Inventive Example C (anionic) was deemed to be third best, and Comparative Example D (cationic) was deemed to be the worst effective at cleansing than the other samples tested.

Example 2

Cleansing With A Gaseous Material

A biphasic composition (excluding air) was prepared and compared with a triphasic cleansing composition (including air) to determine the effectiveness in cleansing skin. The triphasic composition used was Inventive Composition A described above including air. The biphasic composition was Inventive Composition A, but was de-aerated. Therefore, the absence or presence of air was the only difference between the triphasic and biphasic compositions. The biphasic composition used in this Example was de-aerated by centrifugation.

Figure 2C:
FIGS. 2A-2C are a series of photographs depicting the test conducted in Example 2.
Figure 2B:
Figure 2A:
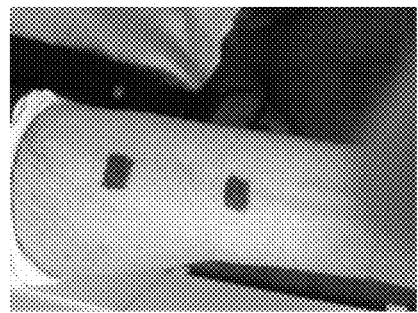

This test was intended to determine whether inclusion of air into a biphasic composition would improve the cleansing ability of the composition. A human subject provided two target skin surfaces on the same arm, so that equal comparisons could be made. The test is depicted in the photographs seen in FIGS. 2A-2C. The two skin test areas were covered with waterproof eye make-up (black shade) and each was allowed to dry for 10 minutes. FIG. 2A depicts the first stage of the test, with placement of the make-up at two test regions on the arm.

About 0.1 cc of the biphasic composition was applied to one of the designated test sites, and about 0.1 cc of the triphasic composition was applied to the second designated test site. Each test area was fully covered with the respective cleansing composition, using the contralateral index finger for five revolutions. Visual observations and feel/touch observations were made and recorded. An additional five revolutions were performed on each test site using the same contralateral index finger, and visual observations and feel/touch observations were again made and recorded.

Determination and evaluation of the cleansing effect of the compositions was determined by visual examination and by feel/touch observation. FIG. 2B shows the results of the test conducted after ten rotations at the test site with the triphasic composition (e.g., including air). FIG. 2C shows the results of the test conducted after ten rotations at the test site with the biphasic composition (e.g., without air).

The triphasic, inventive example, was shown to be more effective at removing make-up in a small-scale (n=5) POP, both by visual evaluation and by skin feel. In all cases, the inventive example (triphasic, e.g., with air) was observed by the study coordinator to be both more effective at removing make-up as well as creating a more pleasant in use experience as compared to the same formulation that is deaerated (the biphasic, e.g., without air). All study participants also perceived the triphasic product to be more effective and more pleasant to use than the biphasic product, as it not only removed more of the make-up, but left less residue on skin after product use.

The cleansers were applied without the use of water to cleanse the skin, thereby demonstrating that the inventive triphasic product can be used without water, as an on-the-go, effective cleanser. Therefore, one method of use of the present invention is to cleanse skin by application of a triphasic composition, without adding additional water during the cleansing process. The triphasic composition itself may include water therein, but the aforementioned method may be used to cleanse skin without added water beyond that contained in the triphasic composition itself. Of course, water or other liquid may be used to aid in cleansing the skin during or after the application and removal of the triphasic composition.

What is claimed is:

1. A cleansing composition comprising:
   a. a first liquid component, comprising an anionic or nonionic surfactant;
   b. a first solid component, comprising a plurality of regenerated cotton particles treated with a hydrophobic coating agent, wherein said regenerated cotton particles are generated from cloth or nonwoven materials previously formed from cotton plant or cotton fibers; and
   c. a first gaseous component, wherein the cleansing composition comprises about 5% to about 40% gaseous component mixed or embedded within the cleansing composition;
   wherein the first liquid component, the first solid component and the first gaseous component are mixed with each other to provide a homogeneous cleansing composition.

2. The cleansing composition of claim 1, wherein the first liquid component comprises an anionic surfactant.

3. The cleansing composition of claim 2, wherein the anionic surfactant is selected from the group consisting of alkyl sulfates; alkyl ether sulfates; alkyl monoglyceryl ether sulfates;
   alkyl monoglyceride sulfates; alkyl monoglyceride sulfonates; alkyl sulfonates; alkylaryl sulfonates; alkyl sulfosuccinates; alkyl ether sulfosuccinates; alkyl sulfosuccinamates; alkyl amidosulfosuccinates; alkyl carboxylates; alkyl amidoethercarboxylates; alkyl succinates; fatty acyl sarcosinates; fatty acyl amino acids; fatty acyl taurates; and fatty alkyl sulfoacetates; alkyl phosphates.

4. The cleansing composition of claim 1, wherein the first liquid component comprises a nonionic surfactant.

5. The cleansing composition of claim 1, wherein the plurality of cotton particles have an average length of about 50 microns to about 700 microns.

6. The cleansing composition of claim 5, wherein the plurality of cotton particles have an average width of about 1 micron to about 50 microns.

7. The cleansing composition of claim 1, wherein the first gaseous component comprises air.

8. The cleansing composition of claim 1, wherein the first liquid component and the first solid component are present in a ratio (volume:weight) of about 1:20 to about 20:1.

9. A method of using a cleansing composition to remove at least one undesired skin element, comprising the steps of:
   a. applying to a target site of the skin surface a composition comprising:
      i. a first liquid component, comprising an anionic or nonionic surfactant;
      ii. a first solid component, comprising a plurality of regenerated cotton particles, wherein said regenerated cotton particles are generated from cloth or nonwoven materials previously formed from cotton plant or cotton fibers; and
      iii. a first gaseous component, wherein the cleansing composition comprises about 5% to about 40% gaseous component mixed or embedded within the cleansing composition;
      wherein the first liquid component, the first solid component and the first gaseous component are mixed with each other to provide a homogeneous cleansing composition;
   b. rubbing the composition on the target site of the skin surface for to remove the undesired skin element and cause the composition to agglomerate into clumps; and
   c. rubbing the agglomerated composition so as to remove the agglomerated composition from the skin surface.

10. The method of claim 9 without the use of water or a liquid rinsing agent to cleanse the composition off of the target site of the skin surface.

11. A method of making a cleansing composition comprising the steps of:
   a. mixing a first liquid component comprising an anionic or nonionic surfactant with a first solid component, comprising a plurality of regenerated cotton particles to form a biphasic composition, wherein said regenerated cotton particles are generated from cloth or nonwoven materials previously formed from cotton plant or cotton fibers; and
   b. mixing a first gaseous component into the biphasic composition to form a triphasic composition, wherein the cleansing composition comprises about 5% to about 40% gaseous component mixed or embedded within the cleansing composition;

wherein the triphasic composition is a homogeneous cleansing composition.

\* \* \* \* \*